March 13, 1956 T. E. MOTOSE Plant Pat. 1,460
ROSE PLANT
Filed April 19, 1955
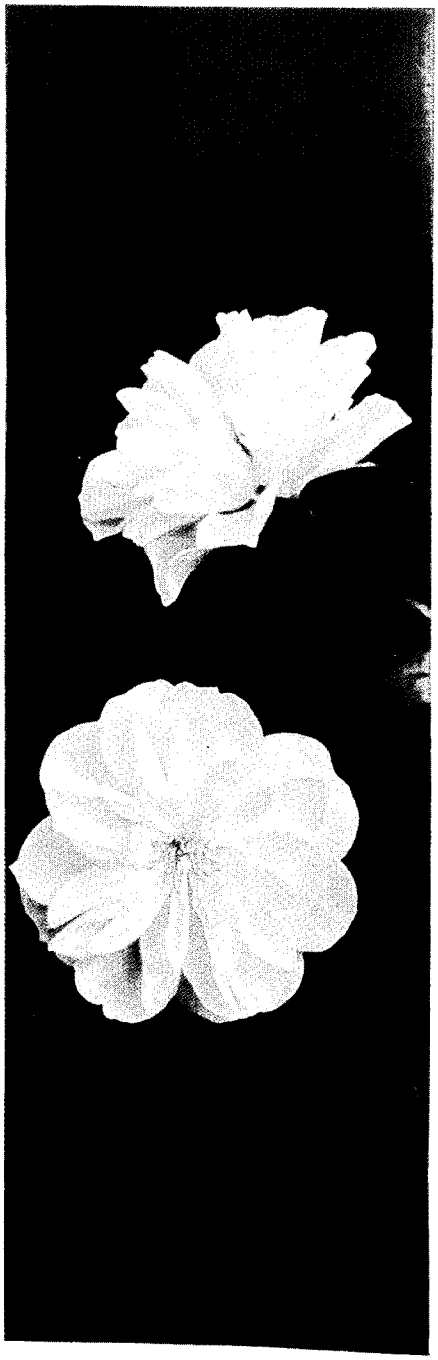
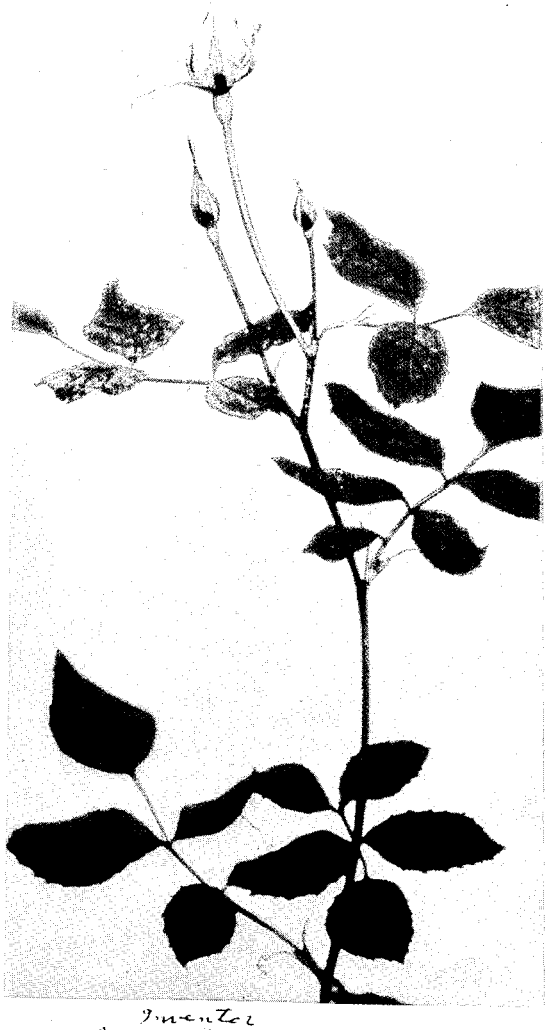
Inventor
Thomas Edison Motose United States Patent Office Plant Pat. 1,460
Patented Mar. 13, 1956

1,460

ROSE PLANT

Thomas Edison Motose, Fairport, N. Y.

Application April 19, 1955, Serial No. 502,537

1 Claim. (Cl. 47—61)

The present invention relates to a new and distinct variety of hybrid polyantha rose, originating as a cross between a seedling of the known variety Garnette (not patented) and a sport of the known variety Summer Snow (Plant Patent No. 416).

The rose Garnette, a hybrid polyantha, has thorns, but the seedling thereof used as a parent of the present invention has very few thorns. The rose Summer Snow, also a hybrid polyantha, has very small quantity of thorns, but the sport thereof used as a parent of the present invention is almost thornless. The said seedling and the said sport were crossed for the purpose of producing a thornless rose plant of the hybrid polyantha class bearing blooms different in shape and color from those of the standard or conventional type of roses, and having the highly desirable recurrent or continuous blooming characteristic.

The objective of the cross was fully attained after numerous trials as shown by the following distinctive and distinguishing characteristics of the new variety, the present invention:

(*a*) Canes, branches, stems and other parts of the plant without any thorn.

(*b*) Recurrent or continuous blooming characteristic.

(*c*) Flowers with delicate coloring similar to that of apple blossom and different in shape from those of the standard or conventional type of roses.

(*d*) Long lasting quality of bloom, which attains its most beautiful stage when fully opened.

The combination of the above characteristics of this new variety distinguishes it from its parents and all other hybrid and species roses known to me.

The above distinguishing characteristics, and the combination thereof, of the new variety have been found to be established definitely and to hold true through succeeding asexual propagations or reproductions. Buddings, cuttings and graftings of the new variety were successfully performed in Fairport, N. Y., in greenhouses and outdoors, and in all seasons.

The accompanying drawing (leaves) and photograph (flowers, buds and stem) of the new variety show the shape and colors of the various parts of the plant. There is very little or no differentiating features in the very young leaves and immature buds.

The place where, and the time when, observations made for the specific purpose of compiling data for this specification: Fairport, N. Y., September 1954.

The following is a detailed description of this new variety of rose, with color terminology in accordance to Ridgway's Color Standard and nomenclature (when plate number is given with the name) or accordance to the generally accepted meaning of Webster's Standard Dictionary (when no plate number is given):

(1) PARENTAGE

A seedling of Garnette seedling (seed parent) and a sport of Summer Snow (pollen parent).

(2) CLASSIFICATION

*Botanical.*—Hybrid polyantha.

*Commercial.*—Floribunda.

(3) PLANT

*Shape.*—Bushy and well branched.

*Growth.*—Vigorous and fast growing as the parent strains.

*Height.*—About one and a half feet under normal outdoor culture in Fairport, N. Y., and frequently exceeding three feet in greenhouses.

(4) CANES AND STEMS

*Older canes or old wood.*—Smooth and thornless, Cress Green (Plate 31) in color.

*New canes or new wood.*—Smooth and thornless, Hay's Russet (Plate 14) in color.

*Very young stem.*—Thornless.

(5) FOLIAGE

*Number.*—3 to 5 leaflets to each leaf-unit, and rarely exceeding that number.

*Quantity.*—Medium.

*Size.*—Small.

*Shape of individual leaflets.*—Generally ovate (terminal leaflets), ovate and ovate-acuminate (the rest of the leaflets).

*Texture.*—Leathery (upper side) and almost smooth (under side).

*Ribs and veins.*—Well marked.

*Serration of edge.*—Multiple and sharp.

*Leaf stem.*—Smooth, Absinthe Green (Plate 31).

*Stipules.*—Medium length, slightly bearded.

*Leaf color.*—Older foliage: Forest Green (Plate 17) on the upper side and Light Elm Green (Plate 17) on the under side; younger foliage: Light Elm Green on both sides with a slight overcast of Oxblood Red (Plate 1).

(6) FLOWER BUD

*Size.*—Small.

*Form.*—Ovoid and frequently pointed.

*Sepals.*—Serrated, Biscay Green (Plate 17) in color inside and Light Bice Green (Plate 17) outside; curl back when petals begin to unfurl.

*Calyx.*—Small in size, Biscay Green (Plate 17) in color.

*Peduncle.*—Short, slender and slightly rough; Biscay Green (Plate 17) in color.

*Color of visible part of petals when sepals begin to divide.*—White (Plate 53) lightly overcast with greenish-yellow.

(7) BLOOM

*Opening.*—Opens up well in most weather conditions.

*Life span.*—Long lasting both on the bush and as cut-flower in vase; easily retains its good coloration for a week or more.

*Size.*—Medium, averaging to 2½ inches in diameter.

*Borne.*—Singly and in clusters on strong stems.

*Form.*—Slightly cupped when first opened and flattens out when fully unfurled, resembling in general pattern, but not in size, that of a double form of crab-apple blossom.

*Petalage.*—Double, 30 or more or less in number under normal condition, the outer petals being larger and becoming smaller toward the center.

*Color of central area.*—White (Plate No. 53) overcast with light pink resembling the pinkness of the regular McIntosh apple blossom.

*Color of the outer area.*—White (Plate No. 53) overcast with light pink resembling the pinkness of the regular Baldwin's apple blossom.

*General color viewed from a distance.*—The color of an average apple blossom.

*Fragrance.*—Very light hybrid-tea rose scent.

*Discoloration.*—Retains the general apple blossom coloring for about a week after opening, and gradually turning into almost white thereafter.

*Most beautiful stage.*—Attains its most beautiful stage when fully opened, which fact is one of the several important features which differentiate this new variety from many other roses which usually attain their greatest beauty for a short period when they are partly opened.

(8) PETALS

*Shape.*—Outer petals: oval; inner petals and petaloids: ovate and lanceolate in forms.

*Arrangement.*—Irregular.

*Persistence.*—Sometimes drop off cleanly, and at other times cling—depending on weather conditions.

*Color of upper surface of outer petals.*—White (Plate 53) overcast with the pinkness of that of the regular or standard Baldwin's apple blossom.

*Color of upper surface of inner petals and petaloids.*—White (Plate 53) overcast with the pinkness of that of the regular or standard McIntosh apple blossom.

*Color of under surface of outer petals.*—White (Plate No. 53) and rarely overcast with pink.

*Color of under surface of inner petals and petaloids.*—White (Plate No. 53) and almost always overcast with general apple blossom pink.

*Thickness.*—Medium.

*Appearance.*—Inside—satiny; outside—shiny.

*Texture.*—Smooth.

(9) GENITAL ORGANS

*Anthers.*—Medium in size, few in number, regular in arrangement around styles, and Ochraceous-Buff (Plate 15) in color.

*Filaments.*—Short in length and light yellow or Sulphur Yellow (Plate 5) in color.

*Pollen.*—Small in quantity and Martius Yellow (Plate 4) in color.

*Styles.*—Short and of uneven height and separated.

*Ovaries.*—Enclosed.

*Stigmas.*—Few in number and Light Dull Green Yellow (Plate 17) in color.

(10) DIFFERENTIATING CHARACTERISTICS

Color of the new variety is not, by itself, the major differentiating characteristic, since weather, soil and other environmental conditions cause it to undergo perceptible changes. The color of the new variety is the one described in specific words in the foregoing paragraphs, and not the one that may appear on the surface of the accompanying drawing or photograph in the future years although the best available oil and pigments have been used thereon.

The absence of thorns from its canes, branches and stems, the recurrent or continuous blooming habit, the long lasting quality of the bloom which attains its most beautiful stage when fully opened, together with the general apple blossom coloring of the bloom as described in the foregoing, in their combination, make this new variety different from the rest of the existing rose-plant.

(11) DISEASE RESISTANCE

The new variety is very resistant to mildew and blackspots under normal weather conditions of Fairport, N. Y.

I claim:

A new and distinct variety of rose plant of the hybrid polyantha class, characterized as to novelty by the general apple-blossom coloring of its flowers, by the long lasting quality of the flowers which reach their most beautiful stage when fully opened, its recurrent or continuous blooming habit, by the absence of thorns from its canes, branches and stems, substantially as described and shown hereinabove and in the accompanying drawing.

No references cited.